(12) United States Patent
Kawakatsu

(10) Patent No.: US 6,769,804 B2
(45) Date of Patent: Aug. 3, 2004

(54) TEMPERATURE MEASURING METHOD, OBJECT DETECTING METHOD AND OBJECT DETECTING DEVICE WITH VIBRATING-TYPE LEVEL SENSOR

(75) Inventor: Hiroshi Kawakatsu, Suita (JP)

(73) Assignee: Nohken Inc., Osaka (JP)

( * ) Notice: Subject to any disclaimer, the term of this patent is extended or adjusted under 35 U.S.C. 154(b) by 0 days.

(21) Appl. No.: 10/461,365

(22) Filed: Jun. 16, 2003

(65) Prior Publication Data

US 2003/0235233 A1 Dec. 25, 2003

(30) Foreign Application Priority Data

Jun. 24, 2002 (JP) .................................... 2002-182554

(51) Int. Cl.[7] .......................... G01F 23/28; G01K 11/22
(52) U.S. Cl. ...................... 374/118; 374/184; 374/45; 73/579; 73/290 V
(58) Field of Search ................. 374/117, 118, 374/184, 183, 185, 163, 45; 73/579, 290 V, 1.82, 1.83, 643, 292, DIG. 1, DIG. 3

(56) References Cited

U.S. PATENT DOCUMENTS

| | | | |
|---|---|---|---|
| 3,164,993 A | * | 1/1965 | Schmidt ...................... 374/184 |
| 3,270,274 A | | 8/1966 | Banks et al. |
| 3,391,576 A | * | 7/1968 | Katsumi ...................... 374/184 |
| 3,421,374 A | * | 1/1969 | Lawrence ................... 374/184 |
| 3,848,466 A | * | 11/1974 | Dial et al. .................... 374/147 |
| 4,740,726 A | * | 4/1988 | Umezawa .................. 73/290 V |
| 4,897,584 A | * | 1/1990 | Grutzmacher et al. ...... 374/184 |
| 5,150,617 A | * | 9/1992 | Schwarz et al. ............... 73/579 |
| 5,247,832 A | * | 9/1993 | Umezawa et al. ......... 73/290 V |
| 5,332,966 A | | 7/1994 | Berberich |
| 6,105,425 A | * | 8/2000 | Kawakatsu ................ 73/290 V |
| 6,642,722 B2 | * | 11/2003 | Raffalt et al. ................ 324/635 |
| 2002/0057094 A1 | | 5/2002 | Raffalt et al. |

FOREIGN PATENT DOCUMENTS

| | | | |
|---|---|---|---|
| EP | 949489 A1 | * 10/1999 | ........... G01F/23/22 |
| GB | 1016858 | 1/1966 | |
| JP | 01232218 | 9/1989 | |
| JP | 11351944 | 12/1999 | |
| WO | WO 200290900 A1 | * 11/2002 | ........... G01F/23/22 |

OTHER PUBLICATIONS

Kawakatsu, H, Derwent–Acc–No: 2003–019735, Abstracted–Pub–No: WO 200290900A, (2004).*

* cited by examiner

*Primary Examiner*—Diego Gutierrez
*Assistant Examiner*—Stanley J. Pruchnic, Jr.
(74) *Attorney, Agent, or Firm*—McDermott Will & Emery LLP

(57) ABSTRACT

A magnet is provided to a vibrating plate within a detection pipe unit and an electromagnet is placed opposite to the magnet with a slight gap therebetween. A drive circuit applies, to a coil at every predetermined measurement cycle, an alternating current at a frequency which is swept over a predetermined range centered at a resonance frequency of the vibrating plate. When the alternating current is applied, a phase comparison circuit detects a change in phase that is caused according to whether or not an object contacts the vibrating plate. A microcomputer determines presence/absence of the object based on the detected change in phase, measures the temperature based on the detected change in phase in a former half cycle of the predetermined measurement cycle and changes the swept frequency based on the result of measurement of the temperature in a latter half cycle of the predetermined cycle.

6 Claims, 10 Drawing Sheets

TEMPERATURE MEASURING METHOD, OBJECT DETECTING METHOD AND OBJECT DETECTING DEVICE WITH VIBRATING-TYPE LEVEL SENSOR

BACKGROUND OF THE INVENTION

1. Field of the Invention

The present invention relates to a temperature measuring method, an object detecting method and an object detecting device with a vibrating-type level sensor. In particular, the present invention relates to a temperature measuring method, an object detecting method and an object detecting device with a vibrating-type level sensor which detects presence/absence of a target object based on an oscillation frequency of a coil of an electromagnet placed opposite to a magnet with a slight gap therebetween, the magnet being provided to a vibrating plate within a detection pipe.

2. Description of the Background Art

FIG. 10A is a schematic block diagram of a conventional vibrating-type level sensor disclosed in Japanese Patent Laying-Open No. 11-351944. Referring to FIG. 10A, a detection pipe unit 1 has its base 11 which is a fixed end and has its leading end closed with a closing unit 12 that is a free end. Within detection pipe unit 1, a thin rectangular vibrating plate 2 is provided. Vibrating plate 2 has one end fastened to closing unit 12 of detection pipe unit 1 and has the other end provided with a permanent magnet to serve as a free end. Accordingly, detection pipe unit 1, closing unit 12 and vibrating plate 2 constitute a folded cantilever in such a manner that detection pipe unit 1 is folded back at closing unit 12 to form a folded section which is vibrating plate 2.

In addition, an electromagnet 4 is attached closely to the inner wall of detection pipe unit 1 to face vibrating plate 2 in the direction of axis thereof. Electromagnet 4 is driven by an alternating current to generate a magnetic field. Between this magnetic field and a magnetic field of permanent magnet 3, an attracting/repelling action is produced to cause oscillation of the folded cantilever having vibrating plate 2, closing unit 12 and detection pipe unit 1 with base 11 serving as the fixed end.

A distortion detecting element 5 is provided on the inner wall at base 11 of detection pipe unit 1. Distortion detecting element 5 detects the state of oscillation amplitude at base 11 of detection pipe 1 to convert the oscillation amplitude into an electric signal and supply the electric signal to an amplifier circuit 6. Amplifier circuit 6 amplifies the supplied signal and provides the amplified signal again to electromagnet 4.

FIGS. 10B and 10C show attracting and repelling forces between electromagnet 4 and permanent magnet 3 caused by a current applied to electromagnet 4. Suppose that there is a relation as shown in FIG. 10B between the polarity of the current applied to electromagnet 4 and a magnetic field generated on electromagnet 4. Then, the pole of electromagnet 4 that faces permanent magnet 3 is the north pole and thus an attracting force is generated between this north pole and the south pole of permanent magnet 3 attached to vibrating plate 2 while a repelling force is generated between the north pole of electromagnet 4 and the north pole of permanent magnet 3. Consequently, the free end of vibrating plate 2 is forced and displaced upward in FIG. 10B.

On the contrary, suppose that the current applied to electromagnet 4 has the opposite polarity. Then, as shown in FIG. 10C, the pole of electromagnet 4 that faces permanent magnet 3 is of the opposite polarity, i.e., the south pole. Accordingly, this south pole repels the south pole of the permanent magnet of vibrating plate 2 while the south pole and the north pole of the permanent magnet attract each other so that the free end of vibrating plate 2 is forced downward to cause a change in oscillation state. In this way, the polarity of the current applied to electromagnet 4 can be changed according to the natural frequency of the vibrating system of the folded cantilever to produce and sustain oscillation.

According to the example shown in FIG. 10A, the oscillation of the vibrating system is detected by detecting element 5 and then converted into an electric signal which is amplified by amplifier circuit 6 and supplied again to electromagnet 4, while a detecting circuit 7 outputs a detection signal. A piezoelectric element or acceleration pickup may be employed as oscillation detecting element 5. The piezoelectric element, however, has problems in that the piezoelectric element is brittle, the piezoelectric element attached to the detection pipe with an adhesive is susceptible to environment and temperature characteristics, and thus the reliability of the piezoelectric element itself is low.

Another method, for example, disclosed in Japanese Patent Laying-Open No. 1-232218 uses a vibrating-type level detection device. This vibrating-type level detection device includes a vibrating body having an exciting piezoelectric element and a receiving piezoelectric element. The vibrating body is excited by the exciting piezoelectric element and resultant oscillation of the vibrating body is detected by the receiving piezoelectric element. An output from the receiving piezoelectric element is input to a bandpass filter which passes an oscillation frequency fa which is a frequency when the vibrating body is not in contact with a target object while the bandpass filter does not pass an oscillation frequency fb which is a frequency when the vibrating body is in contact with the target object. The output from the bandpass filter is then supplied to a voltage comparator circuit to compare the output with a reference voltage. When the vibrating body does not contact the target object, the output from the bandpass filter is lower than the reference voltage. When the vibrating body contacts the target object, the output from the bandpass filter is higher than the reference voltage. The target object can thus be detected.

As for the example of the conventional method, however, the detection circuit has a relatively larger number of components, resulting in problems of a higher cost, a more complicated structure, and increase in assembly steps. Such a large number of components also results in deterioration of the reliability.

SUMMARY OF THE INVENTION

A chief object of the present invention is to provide a temperature measuring method, an object detecting method and an object detecting device with a vibrating-type level sensor by which the number of components can be decreased and the reliability can be improved.

The present invention is a temperature measuring method with a vibrating-type level sensor measuring a temperature by utilizing characteristics of a coil of an electromagnet placed opposite to a magnet with a slight gap therebetween, the magnet being provided to a vibrating plate within a detection pipe. An alternating current at a frequency which is swept over a predetermined range centered at a resonance frequency of the vibrating plate is applied to the coil, and the temperature is measured based on a change in phase angle of a flowing current, the change in phase angle being caused by a change in resistance value of the coil due to a change in temperature of the coil.

Another invention is an object detecting method with a vibrating-type level sensor detecting presence/absence of an object based on an oscillation frequency of a coil of an electromagnet placed opposite to a magnet with a slight gap therebetween, the magnet being provided to a vibrating plate within a detection pipe. An alternating current at a frequency which is swept over a predetermined range centered at a resonance frequency of the vibrating plate is applied to the coil at every predetermined measurement cycle, a change in phase is detected that is caused according to whether or not the object contacts the vibrating plate when the alternating current is applied, presence/absence of the object is determined based on the detected change in phase, a temperature is measured based on the detected change in phase in a former half cycle of the predetermined measurement cycle and, based on a result of measurement of the temperature, the frequency which is swept is changed in a latter half cycle of the predetermined measurement cycle.

Still another invention is an object detecting device with a vibrating-type level sensor detecting presence/absence of an object based on an oscillation frequency of a coil of an electromagnet placed opposite to a magnet with a slight gap therebetween, the magnet being provided to a vibrating plate within a detection pipe. The detecting device includes an alternating current application unit for applying, to the coil at every predetermined measurement cycle, an alternating current at a frequency which is swept over a predetermined range centered at a resonance frequency of the vibrating plate, a phase detection unit for detecting a change in phase caused according to whether or not the, object contacts the vibrating plate when the alternating current is applied by the alternating current application unit, a determination unit for determining presence/absence of the object based on the detected change in phase by the phase detection unit, a temperature measurement unit for measuring a temperature based on a detection output from the phase detection unit in a former half cycle of the predetermined measurement cycle, and a frequency change unit for changing the frequency which is swept, based on a result of measurement by the temperature measurement unit in a latter half cycle of the predetermined measurement cycle.

The phase detection unit detects fluctuation of the phase caused by a beat frequency component generated in the coil of the electromagnet when the oscillation frequency of the vibrating plate and the sweep frequency of the alternating current are combined.

The phase detection unit includes a filter for extracting the beat frequency component.

The temperature measurement unit measures the temperature based on a change in phase angle of a flowing current, the change in phase angle being caused by a change in resistance value of the coil due to a change in temperature of the coil.

As discussed above, with the vibrating-type level sensor according to the present invention, an alternating current at a frequency which is swept over a predetermined frequency range centered at a resonance frequency of the vibrating plate is applied to the coil at every predetermined measurement cycle, and whether an object is present or absent is determined based on a change in phase which is caused depending on whether the object contacts the vibrating plate or not. This method of detecting an object can be employed to provide a detection unit formed of only the driving electromagnet and the permanent magnet. Accordingly, since no piezoelectric element and no acceleration pickup for a receiving sensor is required, the number of components can be decreased and the reliability of the device can be improved.

Moreover, the temperature is measured in a former half cycle of the predetermined measurement cycle based on the detected change in phase, and the range over which the frequency is swept is optimized in a latter half cycle thereof based on the measured temperature. Accordingly, the detection device can be enhanced in response.

Further, only the driving electromagnet and the permanent magnet are used as a detection unit for the temperature measuring method. No thermistor for example is newly required and thus the structure can be simplified and the cost can considerably be reduced.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1A:
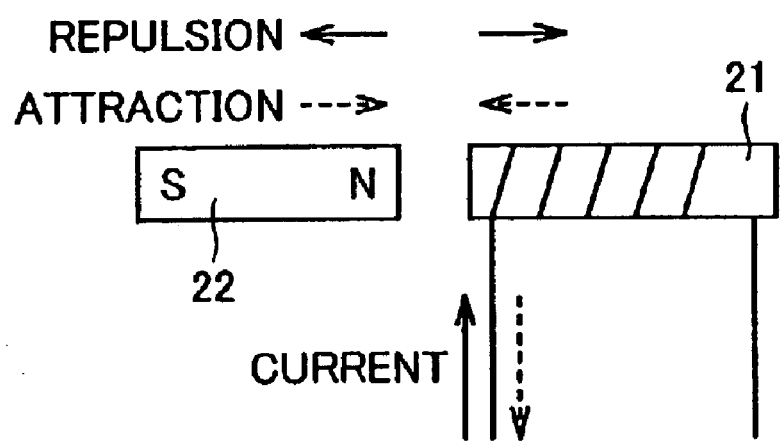
FIGS. 1A and 1B illustrate a principle of a vibrating-type level sensor.

A vibrating-type level sensor according to an embodiment of the present invention is hereinafter described in conjunction with the drawings. It is noted that the same or corresponding components are denoted by the same reference character and description thereof is not repeated here.

Figure 1B:
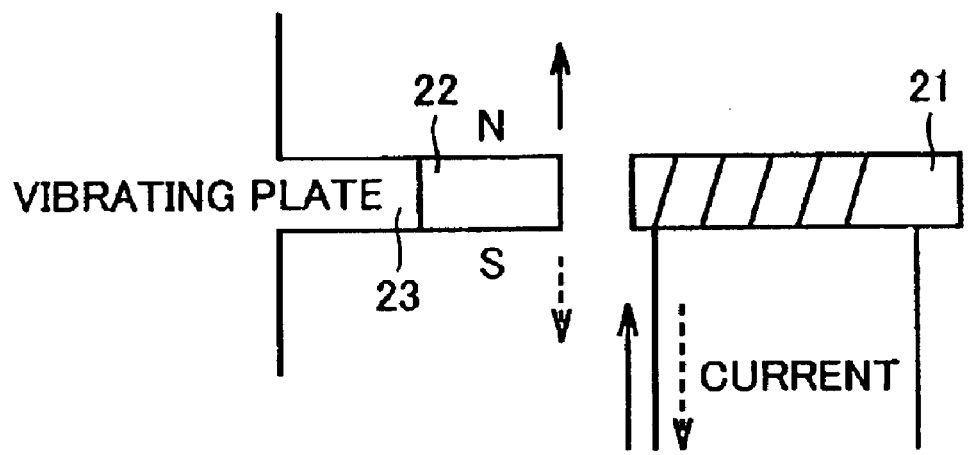

FIGS. 1A and 1B illustrate an operational principle of the vibrating-type level sensor according to the embodiment of the present invention. As shown in FIG. 1A, a rod-shaped electromagnet 21 and a magnet 22 are placed opposite to each other with a slight gap therebetween. As is well-known, the direction of a current flowing through electromagnet 21 is changed to reverse the polarity of electromagnet 21. When the pole of electromagnet 21 and the opposite pole of magnet 22 are the same, a repulsion force is generated and, when different poles are opposite to each other, an attraction force is generated.

This principle is then applied to a vibrating plate 23 of longitudinal vibration type. The direction of polarization of magnet 22 at the leading end of vibrating plate 23 is in the direction of the thickness (the upper pole is the north pole and the lower pole is the south pole in FIG. 1B). Then, an upward/downward force can be applied to magnet 22 by adjusting the direction of the current. Since magnet 22 is located at the free end of vibrating plate 23, the maximum oscillation of vibrating plate 23 is generated by matching the cycle of changing the direction of the current flowing through electromagnet 21 with the resonance cycle of vibrating plate 23. Although the longitudinal vibration mode is essentially a vibration mode of a folded cantilever and is slightly different from the vibration mode of simple vibrating plate 23, these are basically the same.

Figure 10A:
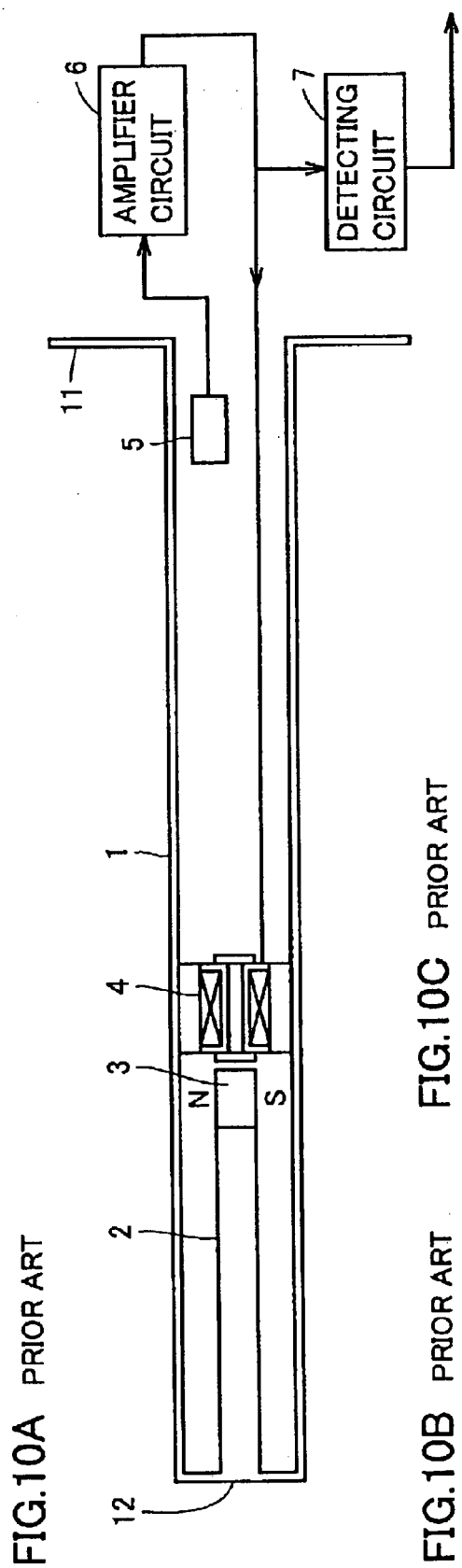
FIG. 10A is a schematic block diagram of a conventional vibrating-type level sensor.
Figure 10C:
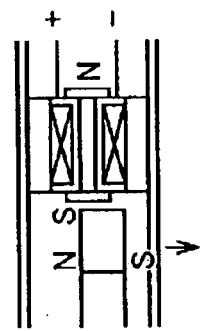
FIGS. 10B and 10C show attracting/repelling forces between an electromagnet 4 and a permanent magnet 3 generated by a current applied to electromagnet 4.
Figure 10B:
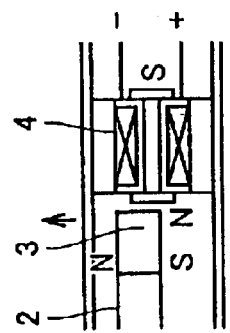

As for the conventional vibrating-type level sensor shown in FIG. 10A, electromagnet 4 serving as a driver and detecting element 5 serving as a receiver are different components. The present invention is characterized in that the driver and the receiver are formed of a common electromagnet.

Figure 2:
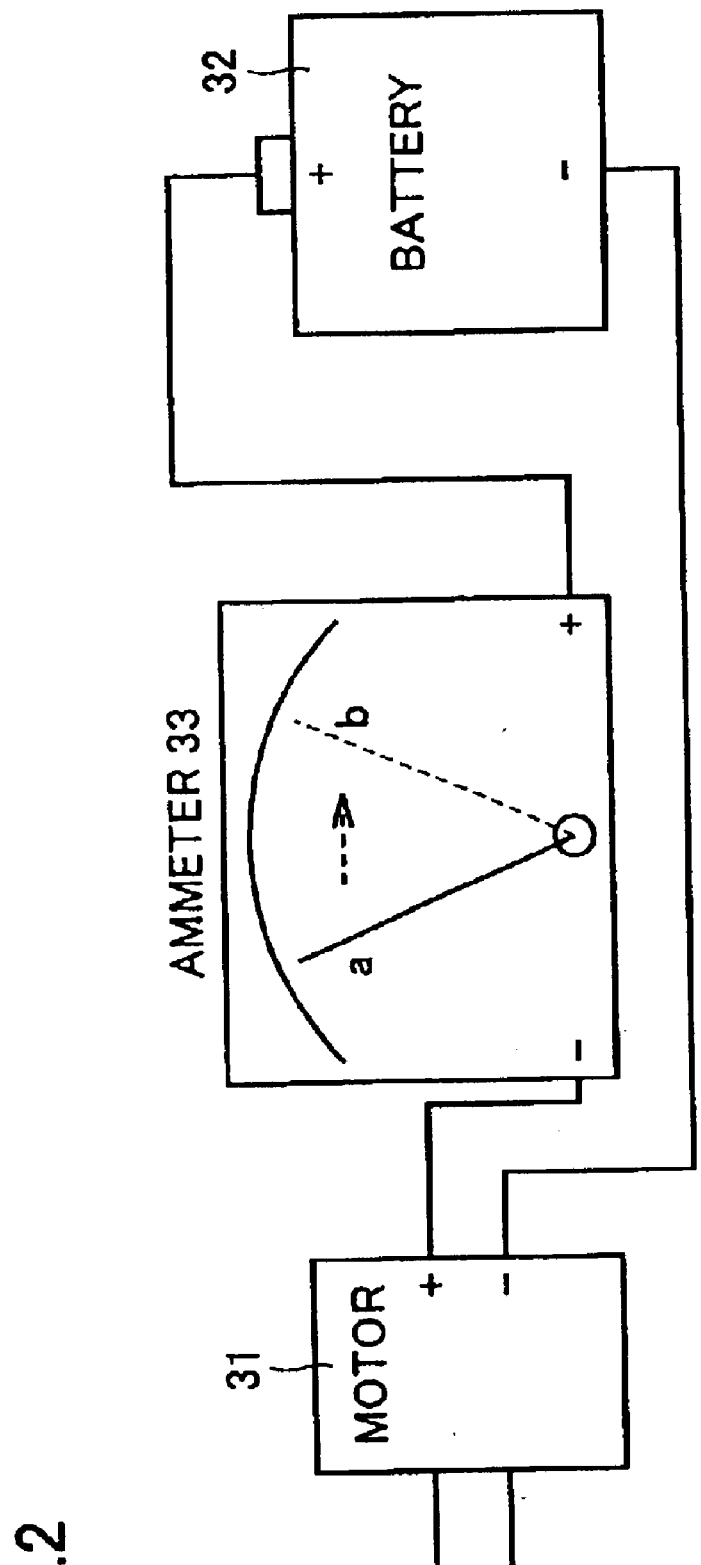
FIG. 2 illustrates a principle of a vibrating-type level sensor according to the present invention.

FIG. 2 illustrates a principle of the vibrating-type level sensor according to the present invention. For example, a power supply which is a battery 32 or the like is connected to a motor 31 to flow a current and rotate motor 31. It is supposed here that a current of "a" flows through motor 31. Then, the rotational axis of motor 31 is grasped in hand to stop the rotation, causing the current flowing through motor 31 to increase to "b" for the following reason. When motor 31 is rotating, rotation of motor 31 generates power to produce a reverse current (power) which restricts the current. When the rotation of motor 31 is stopped, the reverse current (power) disappears and the restricting effect is cancelled.

The vibrating-type level sensor according to the present invention does not have motor 31 as shown in FIG. 2. However, as shown in FIG. 1B, a current is flown through electromagnet 21 to vibrate magnet 22, and then the vibrating magnet 22 generates power which produces a current flowing through electromagnet 21. Accordingly, the drive current can be restricted in a similar way to that as described in connection with motor 31. If a detection unit is covered with powder and thus hindered from vibrating, no power is generated by magnet 22 which is fixed to vibrating plate 23. Then, the drive current flows without being restricted. Accordingly, the drive current can be detected to know the magnitude of vibration and detect presence/absence of powder.

Figure 3:
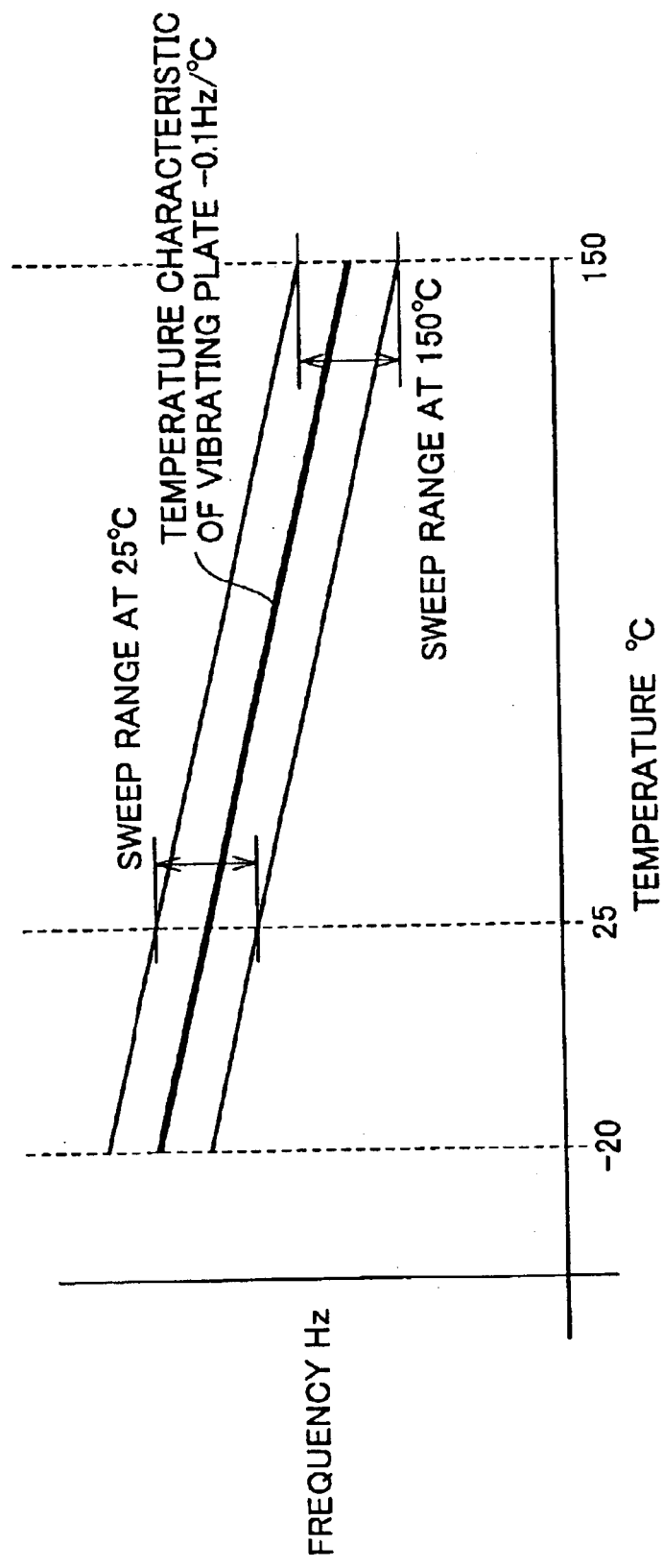
FIG. 3 is a graph showing a relation between sweeping of a frequency and temperature correction.

The vibration of the vibrating-type level sensor is generated by matching the resonance frequency of vibrating plate 23 with the frequency of the drive current. The range of the resonance frequency of vibrating plate 23 is considerably small which is a center frequency of 380 Hz (representative value) ±0.1 Hz. It is impossible to keep the frequency of the drive current within this frequency range. According to the present invention, therefore, the frequency is repeatedly changed (swept) within a certain range from an upper limit through the center frequency to a lower limit as shown in FIG. 3. In this way, the frequency is swept to avoid the possibility that the resonance state cannot be detected.

The resonance frequency of vibrating plate 23 changes with temperature at a rate of approximately −0.1 Hz/° C. and accordingly, the range over which the frequency is swept is temperature-controlled (corrected) according to this rate. In other words, the sweep frequency is corrected to a lower frequency as the temperature increases. The range over which the frequency is swept is 15.7 Hz, i.e. from 9.4 Hz below a reference value to 6.3 Hz above the reference value. Here, the reference value is not the resonance frequency of vibrating plate 23 but a frequency for the peak interference voltage, which is hereinlater described in detail.

The rate at which the frequency is swept is, for example, 11.1 Hz/sec, and thus sweeping over the range of 15.7 Hz is completed in 1.8 second. Although change of the vibration can be observed more thoroughly at a lower sweeping rate, the rate is set at the above-mentioned rate in consideration of the time for measurement.

Figure 4:
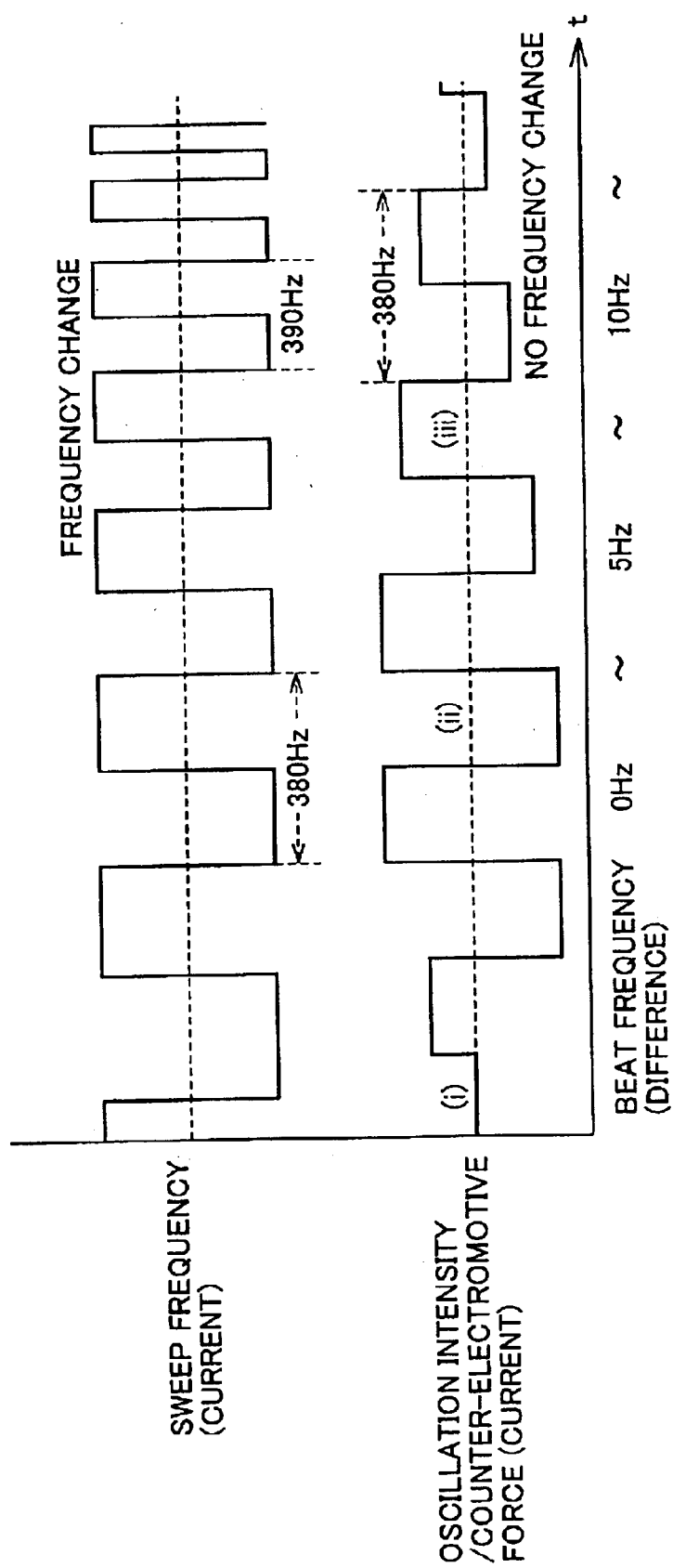
FIG. 4 is a waveform chart illustrating interference voltage (beat).

FIG. 4 is a waveform chart for illustrating the interference voltage (beat). It is known that, when two frequencies are combined, a frequency component corresponding to the sum of the frequencies and a frequency component corresponding to the difference between the frequencies are newly generated. For example, when a frequency of 380 Hz and a frequency of 385 Hz are combined, a frequency component of 765 Hz and a frequency component of 5 Hz are generated.

According to the present invention, as shown in FIG. 3, the frequency is swept over a frequency range of 15.7 Hz from a certain frequency below the resonance frequency to a certain frequency above the resonance frequency, at a rate of 11.1 Hz/sec. As indicated by (i) in FIG. 4, immediately after sweeping is started, no oscillation occurs and thus no counter-electromotive force is produced since there is a great difference between the sweep frequency and the resonance frequency. As indicated by (ii), as the sweep frequency approaches the resonance frequency, the oscillation intensity of vibrating plate 23 becomes greater. When the sweep frequency becomes equal to the resonance frequency, the oscillation intensity reaches the maximum and thus the counter-electromotive force also reaches the maximum. After this, the sweep frequency changes at a certain rate. On the other hand, the oscillation intensity of vibrating plate 23 is gradually attenuated while the oscillation frequency of the vibrating plate is kept at the resonance frequency indicated by (ii), as indicated by (iii).

It is important here that the oscillation frequency does not change in the period in which the oscillation is attenuated as indicated by (iii). Beat frequencies are generated by combination of the changing sweep frequency of the drive current and the constant oscillation frequency of the counter-electromotive force. Of the generated beat frequencies, only the frequency component (which changes) corresponding to the difference is extracted by filtering so as to determine whether powder is present or not based on the magnitude of the frequency component.

If the detection unit is covered with powder and accordingly vibrating plate 23 does not oscillate, no counter-electromotive force is generated and no beat frequency is generated. An embodiment of a vibrating-type level sensor using the above-discussed principle is now described in detail.

Figure 5:
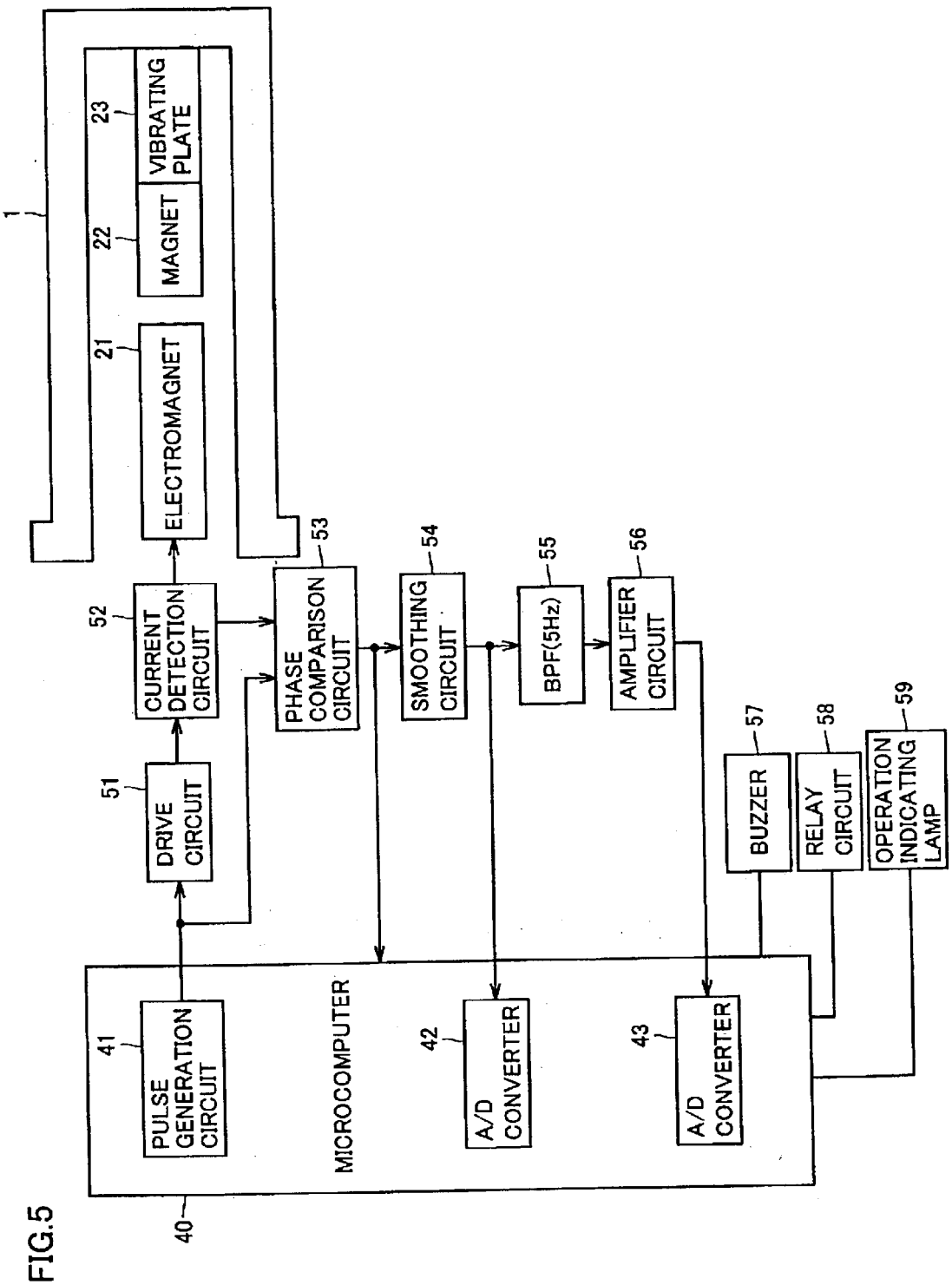
FIG. 5 is a block diagram of a vibrating-type level sensor according to an embodiment of the present invention.

FIG. 5 is a block diagram of the vibrating-type level sensor according to an embodiment of the present invention. Referring to FIG. 5, a microcomputer 40 includes a pulse generation circuit 41 generating a pulse voltage at a sweep frequency, and the generated pulse voltage is applied from a drive circuit 51 through a current detection circuit 52 to electromagnet 21. Current detection circuit 52 detects a pulse current flowing through electromagnet 21 to provide the detected pulse current to a phase comparison circuit 53.

Phase comparison circuit 53 detects a phase difference between the pulse current and the pulse voltage supplied from the pulse generation circuit.

When no powder contacts the detection unit, vibrating plate 23 oscillates and thus the drive current has beat components generated as described above and fluctuation occurs in the output from phase comparison circuit 53. When powder contacts the detection unit, vibrating plate 23 does not oscillate and thus such fluctuation of phase does not occur. The output from phase comparison circuit 53 is provided to a smoothing circuit 54 while being taken as a capture signal by microcomputer 40. Smoothing circuit 54 converts the signal into an analog voltage which is easy to handle, since the output from phase comparison circuit 53 is a kind of PWM signal.

The analogue voltage resultant from conversion by smoothing circuit 54 is supplied to a bandpass filter (BPF) 55 and to an A/D converter 42 of 10 bits incorporated in microcomputer 40 to be converted into a digital signal. This digital signal is used as an input for temperature measurement. BPF 55 detects only a fluctuation (beat) component close to 5 Hz. The detected signal is amplified by an amplifier circuit 56 to be supplied to an A/D converter 43 of 10 bits incorporated in microcomputer 40. The digital signal resultant from conversion by A/D converter 43 is read, as a powder detection signal, at an interval of 2.2 msec into microcomputer 40.

To microcomputer 40, a relay circuit 58 and an operation indicating lamp 59 are connected. Microcomputer 40 performs an operation on the read detection signal to determine the peak value of the signal and compare the peak value with a predetermined set value. Moreover, based on the result of the comparison, microcomputer 40 outputs a signal indicating presence/absence of an object to relay circuit 58 and to operation indicating lamp 59.

When electromagnet 21 is disconnected, microcomputer 40 indicates a temperature value which is normally impossible. Then, this is regarded as an error and an alarm is issued by means of buzzer 57 for example.

According to the above-discussed embodiment, the fluctuation is detected by phase comparison circuit 53. The detection, however, is not limited to this and may be done by other means for detecting a phase difference.

Figure 6:
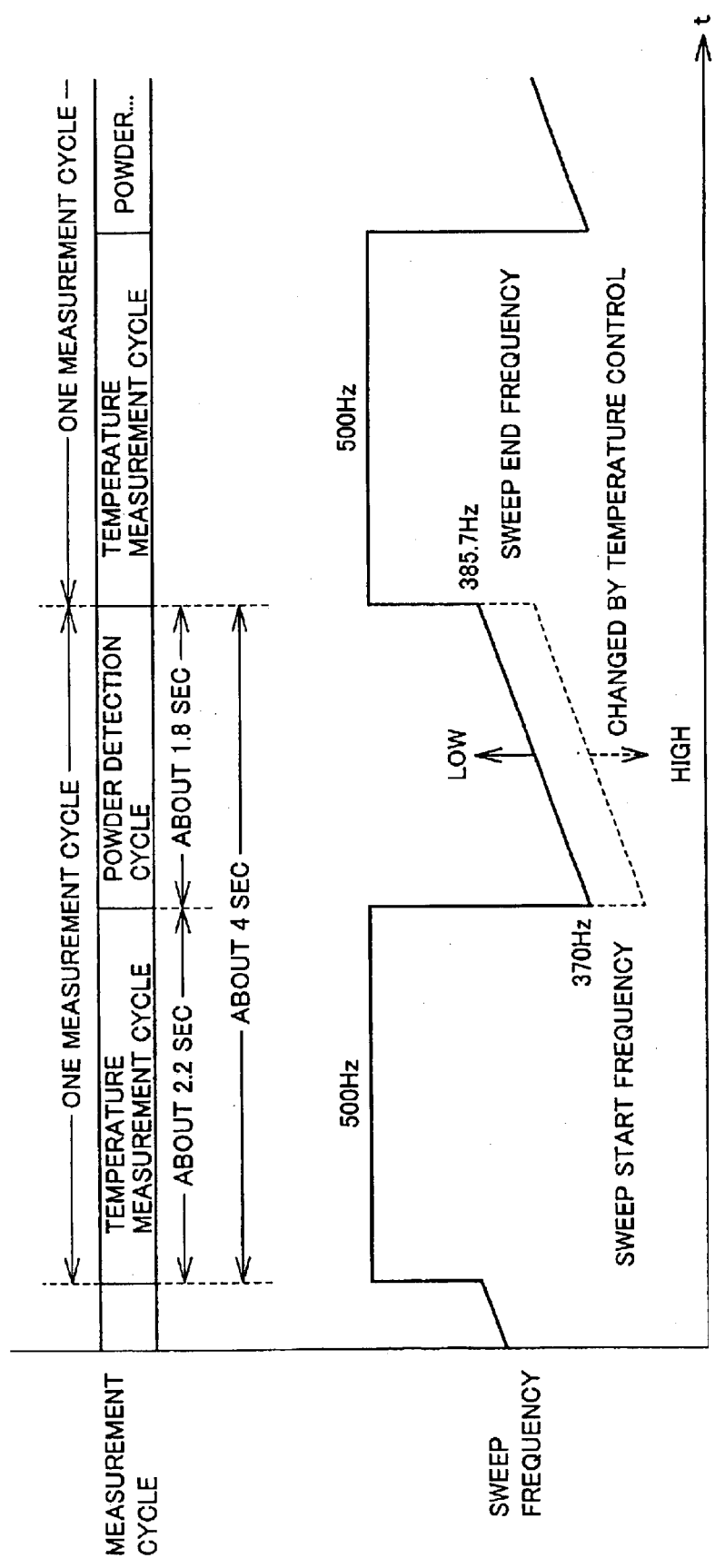
FIG. 6 shows a sequence of measurement with the vibrating-type level sensor shown in FIG. 5.
Figure 7:
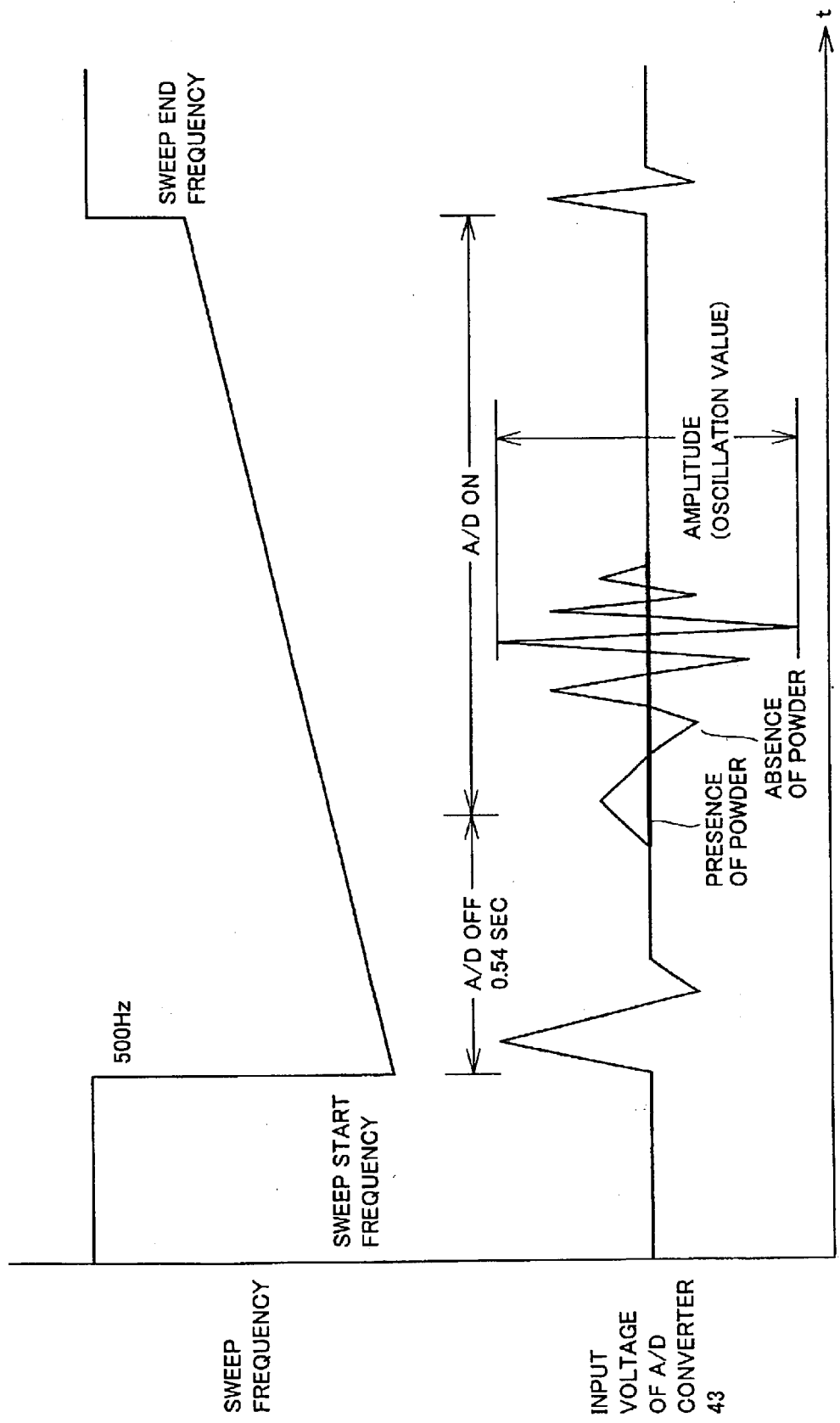
FIG. 7 shows in detail a powder measurement period in the measurement sequence in FIG. 6.

FIG. 6 shows a sequence of measurement with the vibrating-type level sensor shown in FIG. 5, and FIG. 7 shows in detail a powder detection period in the measurement sequence shown in FIG. 6.

Microcomputer 40 takes a level measurement with one measurement cycle of approximately 4 seconds, for example, as shown in FIG. 6. A former half, approximately 2.2 seconds, of the one measurement cycle of approximately 4 seconds, is a temperature measurement cycle, and a latter half thereof of approximately 1.8 seconds is a powder detection cycle. In the former temperature measurement cycle, microcomputer 40 measures a temperature value based on a digital output from A/D converter 42. Then, based on the measured temperature value, microcomputer 40 controls the range over which the frequency is swept in the powder detection cycle.

In the temperature measurement cycle, as shown in FIG. 6, the sweep frequency is fixed at 500 Hz. As shown in FIG. 7, in the period of 0.54 second from the start of the powder detection period, there is an influence of noise of the drive current due to switching from 500 Hz to a sweep starting frequency. Then, in this period, the output from A/D converter 43 is made OFF and no voltage is taken. In a subsequent period, the output from A/D converter 43 is made ON to read a voltage.

When there is no powder, a fluctuation component due to a beat voltage or the like is generated as shown in FIG. 7. When the detection unit is covered with powder for example and no oscillation occurs, no voltage due to fluctuation is generated as indicated by the bold line in FIG. 7. The amplitude of the oscillation is an oscillation value. The oscillation value ranges from 0 to 1023 (10-bit A/ID converter 43).

Figure 8A:
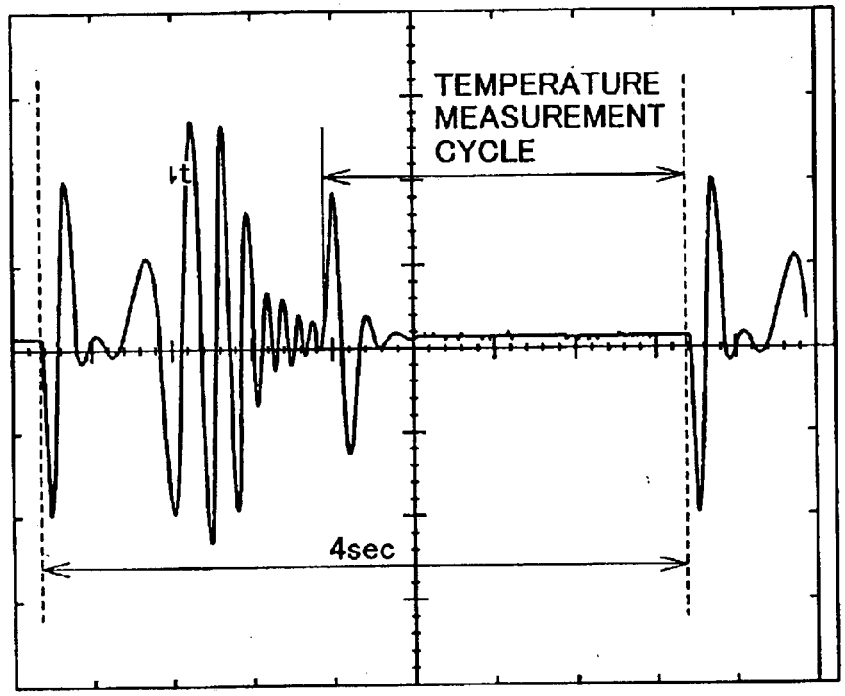
FIGS. 8A and 8B show an input voltage waveform of an A/D converter 43.
Figure 8B:
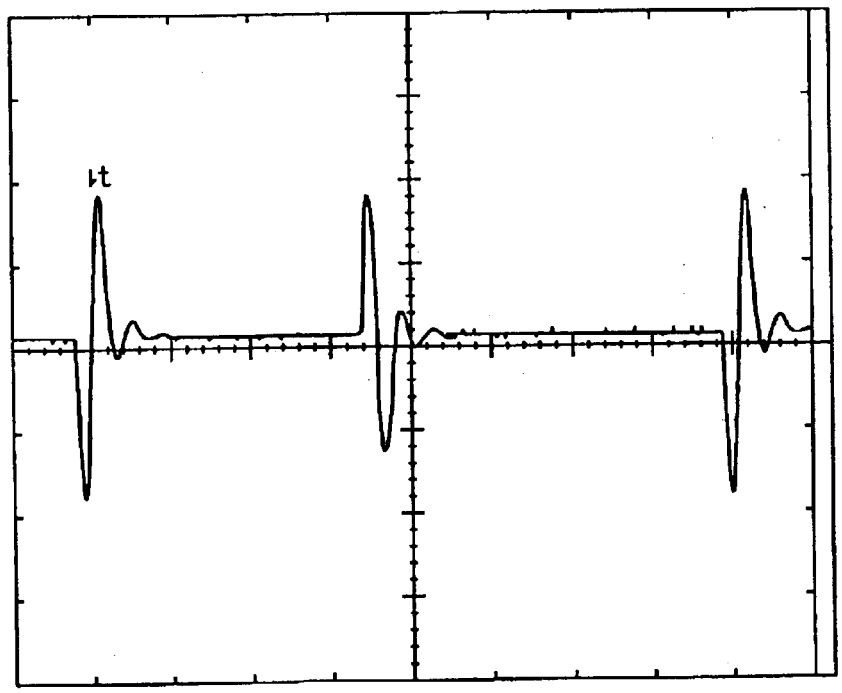

FIGS. 8A and 8B show actual measurements of an input voltage waveform of A/D converter 43 shown in FIG. 7. FIG. 8A shows a waveform which is observed when the leading end of detection pipe unit 1 is free and FIG. 8B shows a waveform which is observed when the leading end of detection pipe unit 1 is grasped in hand. As seen from comparison between FIG. 8A and FIG. 8B, in the former half period, the waveform observed when the leading end of detection pipe unit 1 is free is apparently different from the waveform observed when the leading end is grasped. Therefore, it never occurs that presence/absence of powder is erroneously determined.

Figure 9A:
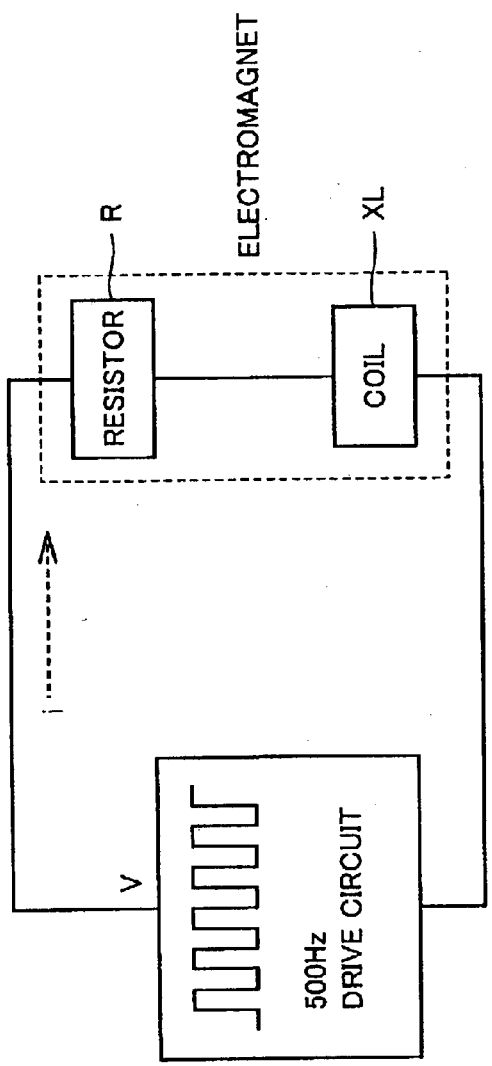
FIGS. 9A and 9B show in detail measurement of temperature with the vibrating-type level sensor shown in FIG. 5.
Figure 9B:
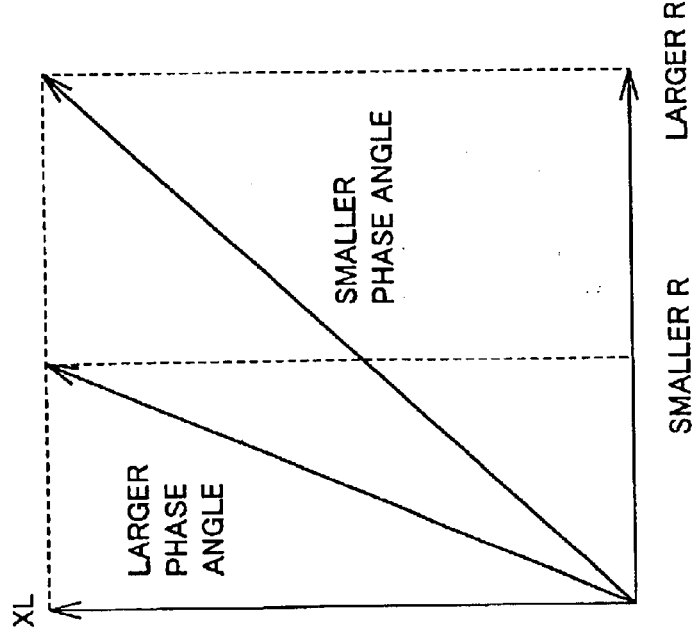

FIGS. 9A and 9B show in detail measurement of temperature with the vibrating-type level sensor shown in FIG. 5. As shown in FIG. 9B, electromagnet 21 includes a coil and is equivalently regarded as a unit having an inductance XL and a resistor R connected in series. An alternating current (pulse) voltage is applied to this circuit and then a current flows in this circuit with a phase lag of inductance XL and resistor R. When the temperature of the coil changes, the resistance changes as described above, however, inductance XL does not change even if the temperature changes. Then, as shown in FIG. 9A, the phase angle of the flowing current changes according the change in resistance due to the change in temperature.

Here, the drive frequency is set at a constant value of 500 Hz in order to avoid influence of mechanical oscillation and eliminate an error due to frequency change. The phase of the current flowing through electromagnet 21 is compared with the phase of reference supplied to drive circuit 51 by phase comparison circuit 53. The output from the phase comparison circuit 53 is converted into a DC voltage according to a phase difference after smoothing circuit 54, and the DC voltage is applied to A/D converter 42. The resolution for the temperature is determined depending on the resolution of A/D converter 42. For the circuit shown in FIG. 5, temperature data changes by one count with respect to a change of approximately 3.3° C.

As the DC component is removed by BPF 55, drive data is not affected by the voltage change due to the temperature change.

The resonance frequency of vibrating plate 23 varies to some degree which is inevitable in terms of manufacture. Moreover, the resonance frequency of long vibrating plate 23 and that of normally-shaped vibrating plate 23 differ from each other. Then, the operating frequency of the detection unit has to be stored in microcomputer 40 after assembly or after replacement of the detecting unit. This operation is called tuning. From temperature data, frequency data and measured temperature data stored in the tuning, a range of a reference (sweep) frequency in measurement is calculated according to the following formula. In this way, an optimum sweep frequency can be determined to take measurements.

$$Fs=(Ts-Tt) \cdot k + Ft$$

Tt: temperature data in tuning
Ts: temperature data in measurement
Ft: frequency data in tuning Fs: reference frequency in measurement k: proportionality constant Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A temperature measuring method with a vibrating-type level sensor measuring a temperature by utilizing characteristics of a coil of an electromagnet placed opposite to a magnet with a slight gap therebetween, the magnet being provided to a vibrating plate within a detection pipe unit, wherein an alternating current at a frequency which is swept over a predetermined range centered at a resonance frequency of said vibrating plate is applied to said coil, and the temperature is measured based on a change in phase angle of a flowing current, said change in phase angle being caused by a change in resistance value of said coil due to a change in temperature of said coil.

2. An object detecting method with a vibrating-type level sensor detecting presence/absence of an object based on an oscillation frequency of a coil of an electromagnet placed opposite to a magnet with a slight gap therebetween, the magnet being provided to a vibrating plate within a detection pipe unit, wherein an alternating current at a frequency which is swept over a predetermined range centered at a resonance frequency of said vibrating plate is applied to said coil at every predetermined measurement cycle, a change in phase is detected that is caused according to whether or not said object contacts said vibrating plate when said alternating current is applied, presence/absence of said object is determined based on said detected change in phase, a temperature is measured based on said detected change in phase in a former half cycle of said predetermined measurement cycle and, based on a result of measurement of said temperature, said frequency which is swept is changed in a latter half cycle of said predetermined measurement cycle.

3. An object detecting device with a vibrating-type level sensor detecting presence/absence of an object based on an oscillation frequency of a coil of an electromagnet placed opposite to a magnet with a slight gap therebetween, the magnet being provided to a vibrating plate within a detection pipe unit, comprising:

alternating current application means for applying, to said coil at every predetermined measurement cycle, an alternating current at a frequency which is swept over a predetermined range centered at a resonance frequency of said vibrating plate;

phase detection means for detecting a change in phase caused according to whether or not said object contacts said vibrating plate when said alternating current is applied by said alternating current application means;

determination means for determining presence/absence of said object based on said detected change in phase by said phase detection means;

temperature measurement means for measuring a temperature based on a detection output from said phase detection means in a former half cycle of said predetermined measurement cycle; and frequency change means for changing said frequency which is swept, based on a result of measurement by said temperature measurement means in a latter half cycle of said predetermined measurement cycle.

4. The object detection device with the vibrating-type level sensor according to claim 3, wherein said phase detection means detects fluctuation of the phase caused by a beat frequency component generated in the coil of said electromagnet when the oscillation frequency of said vibrating plate and the sweep frequency of said alternating current are combined.

5. The object detection device with the vibrating-type level sensor according to claim 4, wherein said phase detection means includes a filter for extracting said beat frequency component.

6. The object detection device with the vibrating-type level sensor according to claim 3, wherein said temperature measurement means measures the temperature based on a change in phase angle of a flowing current, said change in phase angle being caused by a change in resistance value of said coil due to a change in temperature of said coil.

* * * * *